United States Patent
Righi et al.

(10) Patent No.: US 8,564,503 B2
(45) Date of Patent: Oct. 22, 2013

(54) PROTECTIVE SCREEN

(75) Inventors: Aronne Righi, Bologna (IT); Francesco Rambaldi, Bologna (IT)

(73) Assignee: Francesco Rambaldi, Bologna (IT)

( * ) Notice: Subject to any disclaimer, the term of this patent is extended or adjusted under 35 U.S.C. 154(b) by 580 days.

(21) Appl. No.: 12/744,130

(22) PCT Filed: Nov. 13, 2008

(86) PCT No.: PCT/IT2008/000707
§ 371 (c)(1),
(2), (4) Date: May 21, 2010

(87) PCT Pub. No.: WO2009/069166
PCT Pub. Date: Jun. 4, 2009

(65) Prior Publication Data
US 2010/0253603 A1 Oct. 7, 2010

(30) Foreign Application Priority Data
Nov. 30, 2007 (IT) .............................. BO2007A0792

(51) Int. Cl.
*G09G 5/00* (2006.01)
(52) U.S. Cl.
USPC ..................................... 345/8; 345/7; 351/44
(58) Field of Classification Search
USPC ........... 345/7–9, 87, 102; 351/44, 45, 49, 158
See application file for complete search history.

(56) References Cited

U.S. PATENT DOCUMENTS

| | | | |
|---|---|---|---|
| 5,184,156 A | 2/1993 | Black | |
| 5,315,099 A | 5/1994 | Gunz | |
| 5,377,037 A | 12/1994 | Branz | |
| 5,552,841 A | 9/1996 | Gallorini | |
| 6,538,624 B1 * | 3/2003 | Karasawa et al. | 345/8 |
| 2004/0061663 A1 * | 4/2004 | Reynolds et al. | 345/8 |
| 2004/0113867 A1 * | 6/2004 | Tomine et al. | 345/8 |
| 2004/0178970 A1 * | 9/2004 | El Sayed et al. | 345/8 |
| 2005/0128431 A1 * | 6/2005 | Jannard et al. | 351/158 |
| 2005/0280769 A1 | 12/2005 | Cano | |
| 2006/0132382 A1 * | 6/2006 | Jannard | 345/8 |
| 2006/0250574 A1 * | 11/2006 | Grand et al. | 351/158 |
| 2007/0285613 A1 * | 12/2007 | Hobbs | 351/45 |

FOREIGN PATENT DOCUMENTS

GB 2283103 A 4/1995

* cited by examiner

*Primary Examiner* — Kimnhung Nguyen

(57) ABSTRACT

The present invention generally relates to a screen 1 of the type including a visor 2 whit variable transparency as a function of the extent of the electrical values measurable at its power supply clips 3. The visor 2 is power supplied by a respective electric source with the possible interposition of appropriate devices 4 for the control and management of the electrical values of the power supplied. The liquid crystal visor 2 is flexible to be adapted to the surfaces of installation and the electrical power source includes at least a photovoltaic cell 5.

4 Claims, 5 Drawing Sheets

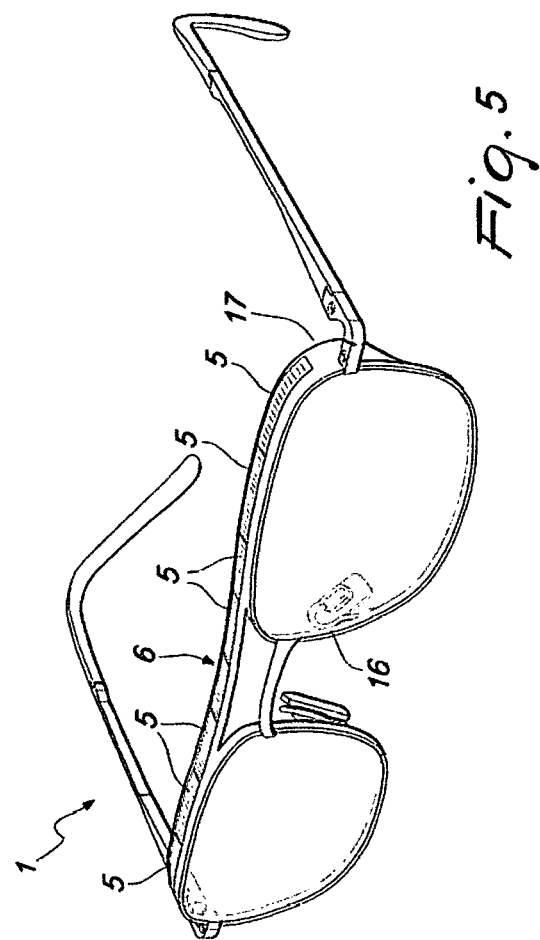

PROTECTIVE SCREEN

TECHNICAL FIELD

It constitutes object of the present invention a screen for eyes that is protective from incident light radiations with a device that can adapt the intensity of the incident beam of light.

BACKGROUND ART

During the passage from a place characterized from strong brightness to one poorly illuminated, and in the opposite case, correspondent to a fast increase of brightness, in the first moments that succeed the passage it is not possible to have a correct perception of the images; this situation is dangerous when driving a vehicle, as the driver may not be able to distinguish eventual obstacles.

The situation in which the driver interposes darkening lenses (for example sunglasses or dark helmet visors) between his eyes and the external environment is much more dangerous: the fast brightness decrease that is noticeable, for example entering a tunnel, can be so hard to prevent the driver from seeing clearly. The eye, as a matter of fact, also if adapting after some time, perceives a light signal attenuated from the presence of the darkening lenses; such lenses, in fact, continue in filtering the light also when is no longer needed. The driver is then forced to eliminate lenses (take off glasses or lift up visor), dangerous act, specially if done at high speed.

In many sports is necessary to protect eyes with screens suitable for acting as a filter towards solar radiations.

In all that cases it's opportune that the screen is suitable in maintaining a filtering action dependent on the features of intensity and of incident angle of the radiation which is subjected to.

The adjustment of the filtering action is usually done dealing with an appropriate control device: in many sports, and when driving, it's not possible to act with the hands on such control devices as they are involved in carrying out gestures relative to the sporting acts and/or to driving.

It's not possible to convert glasses, helmets' visors or traditional screens, completely transparent (and/or with constant and settled colour or darkening level), into screens with a filtering actions dependent on the incident radiation. Actually are available embodied solutions that approximate the result described above, but they are of poor practical interest because of their slowness in transparency variation and their limits in the filtering action.

This impossibility makes all the currently existing and utilized screens substantially unsuitable for overcoming the previously pointed out problems.

DISCLOSURE OF THE INVENTION

It is therefore a technical duty of the present invention to counter above mentioned lacks and to satisfy hinted needs providing a protection screen suitable to perform a filtering action depending on the incident radiation's features.

In this technical duty's field, it is another object of the present invention to provide a protective screen in which the control of transparency is of automatic type.

It is yet another object of the present invention to provide a protective screen that can be applied on other existing and being used screens.

It is still another object of the present invention to perform the previous task with a simple embodiment, of relatively easy practical implementation, of safe use and effective functioning, as well as relatively cheap.

This duty and this scope are reached by the present protective screen which comprises a visor with variable transparency as a function of the extent of the electrical values measurable at its power supply clips, visor which is power supplied by a respective electric source with the possible interposition of appropriate devices for the control and the management of the electrical values of the power supplied. The liquid crystal visor is characterized by the fact of being flexible to be adapted to the surface of installation and by the fact that the power source includes at least a photovoltaic cell.

BRIEF DESCRIPTION OF THE DRAWINGS

Further details will ensue more clear and evident from the detailed description of an embodiment (implementation) that is preferred, but not exclusive, of a protective screen according to the invention, instanced as a sample in the attached drawings, in which:

FIG. 5 visually represents, in a schematic prospective view, a couple of protective screen, according to the invention, included in a pair of glasses.

BEST MODE FOR CARRYING OUT THE INVENTION

Figure 1:
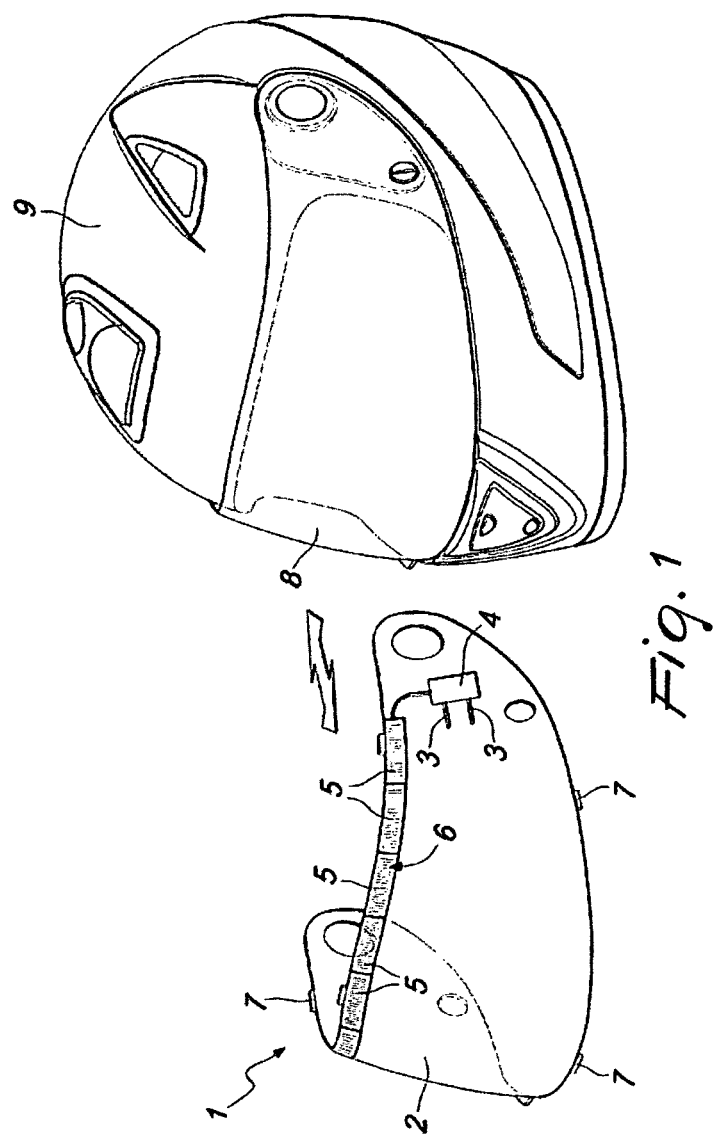
FIG. 1 visually represents, in a schematic prospective view, a protective screen, according to the invention, applicable on a protective helmet.

The screen 1 comprises a visor 2 with variable transparency as a function of the extent of the electrical values measurable at its power supply clips 3.

The visor 2 is power supplied by a respective electric source with the possible interposition of opportune devices for the control and the management of the electrical values of the power supplied.

The visor 2 advantageously is of the liquid crystal type and is flexible to adapt to the surface of installation.

The visor 2 may vary its own transparence as a function of electrical values from a maximum value, correspondent at a completely translucent glass sheet, when the electric voltage (or the amperage or the combination of the two values) is null, to a minimum value of transparency, characterized by a predefined opacity, when the electric voltage (or the amperage or the combination of the two values) is maximum.

The source of electric power comprises at least a photovoltaic cell 5.

In order to obtain an easy and efficient functioning, photovoltaic cells 5 are a pluralism reciprocally interconnected to build a photovoltaic panel with the right power to fully supply the liquid crystal visor 2.

The photovoltaic panel 6 constituted by the cells 5, may be of a completely transparent type; in this case the panel 6 may be substantially overlapped to the visor 2, or coupled with any part of the screen 1 or with one of the surface which the screen 1 have to be coupled.

It's prefigured also the possibility to realize the panel 6 with photo-sensible paint coat of the type having photovoltaic characteristics and then suitable to supply electricity trough at least a couple of clips placed at the extremities of the coat itself with voltage values between them as a function of the incident radiation on it.

Electrical supply parameters of the visor 2 (voltage supply, functioning amperage and power used) are known to the engineer who will choose a panel 6 constituted by a proper number of cells 5 interconnected each others with parallel or serial circuits in order to satisfy the previously said needs.

The visor 2, from a constructive point of view, comprises at least one layer of transparent and flexible material coupled with a crystal liquid unit.

In one embodiment of undoubted practical and applicative interest, the visor 2 comprises a couple of layers of flexible and transparent material to which is interposed a liquid crystal unit: this way the unit is protected against hits and against direct contact with external environment assuring optimal resistance and insensitivity to the installation environment.

The two sheets may be built with Plexiglas, polycarbonate or other translucent and high-deformable materials.

Positively can be adopted also rubbery materials (for example silicone sheets or materials with similar mechanical characteristics) that could assure a perfect stability to the installation surfaces with an electrostatic adhesion or as a consequence of a suction effect.

Opportunely the visor 2 has shape and sizes that match the ones of the surface of installation, and the screen 1 comprises opportune devices 7 to be fixed to the surface itself.

According to one of the possible embodiment of major practical and applicative interest the visor 2 has shape and sizes that match the ones of the visor 8 of an helmet 9 onto which is prefigured the installation of the screen 1 itself. Also in this case the screen 1 has to include opportune devices 7 to be fastened on the surface itself.

In this way a motorcyclist or a pilot could constantly have at his disposal an efficient protection against the luminous incident radiation: for example, at the entrance (or at the exit) of a tunnel, the fast lightness variation creates an initial period of poor clearness in the perception of the images (dazzling and/or excessive darkness). In that cases would be opportune to put on (or to take off) a darkened lens, but this act would force the user to leave hands from the vehicle's controls creating a situation of potential danger.

The apposition of the screen 1 on the visor 8 of the helmet (9) allow the user to have at his disposal a filter (against the incident radiation) with variable value as a function of the intensity of the radiation itself: practically the screen (1) will be completely transparent when the external light is scarce, while will be strongly darkened when the incident radiation is particularly intense.

Accordingly to one embodiment that is alternative, but based on the same constructive and use principle, the visor (2) has sizes and shape that match the at least one lens (10) of goggles (11), of the type that is suitable for being worn before eyes, onto which is prefigured the installation of the screen (1) itself.

Also in this case the screen 1 has to comprise opportune devices (7) to be fastened to the at least one lens 9 itself.

Alternatively is very interesting to prefigure embodiment in which the visor 1 would have sizes and shape that match the one of the at least one lens 12 of glasses 13 onto which is prefigured the installation of the screen (1) itself. The fastening of the screens 1 on the glasses 13 is possible trough opportune fastening device 7.

The advantage, also in that cases described relatively to alternative embodiment, is to be able to have at proper disposition the screens 1 accordingly to the invention onto goggles 11 and onto glasses 13 of standard type make them able to carry out an active filtering action against luminous incident radiation.

An element constituting an electrical charge is putted in a parallel circuit with the power supply clips of the liquid crystal visor 2 in order to rapidly dissipate the energy that was accumulated in the visor 2 restoring the initial conditions when the electric supply is missing.

From a constructive point of view is possible to figure out the use (as electric charge) of a resistor, in parallel circuit with the user, with a fixed or variable value of electric resistance (for example good results are obtained with electric resistors of about 1 M$\Omega$). This component has the scope of immediately discharge the circuit when the current supplied from the solar panel 6 is not enough to correctly supply the visor 2, substantially doing a stabilizing function toward the circuit itself.

It can be prefigured an application of the invention in which the screen 1 could be directly incorporated (during the production) in commonly used elements.

Figure 2:
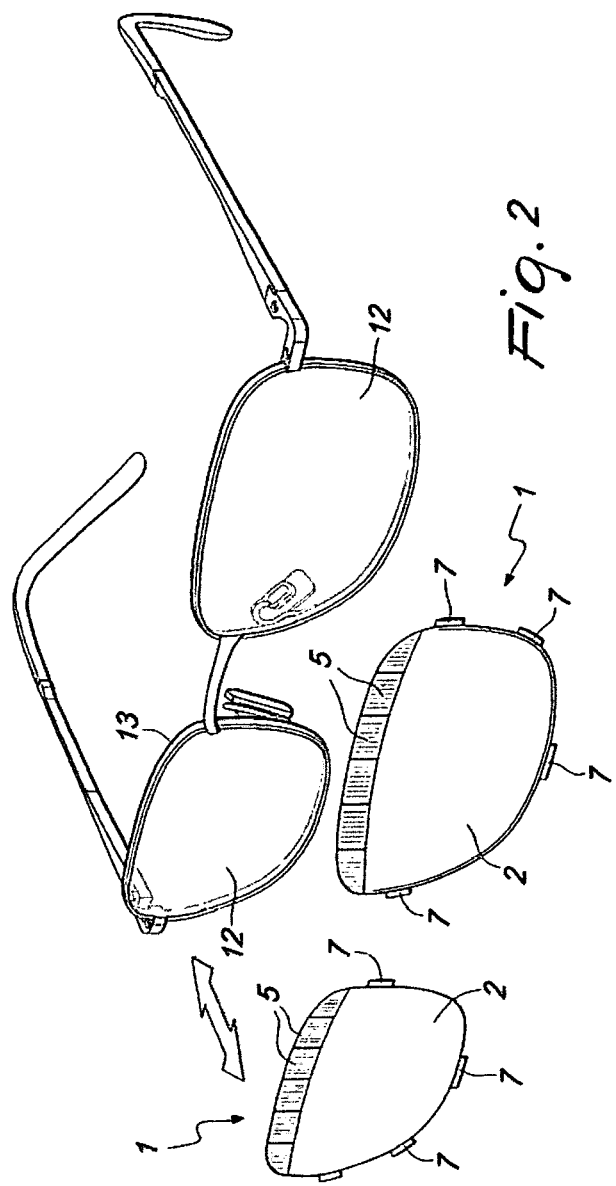
FIG. 2 visually represents, in a schematic prospective view, a couple of protective screens, according to the invention, applicable on a pair of glasses.
Figure 3:
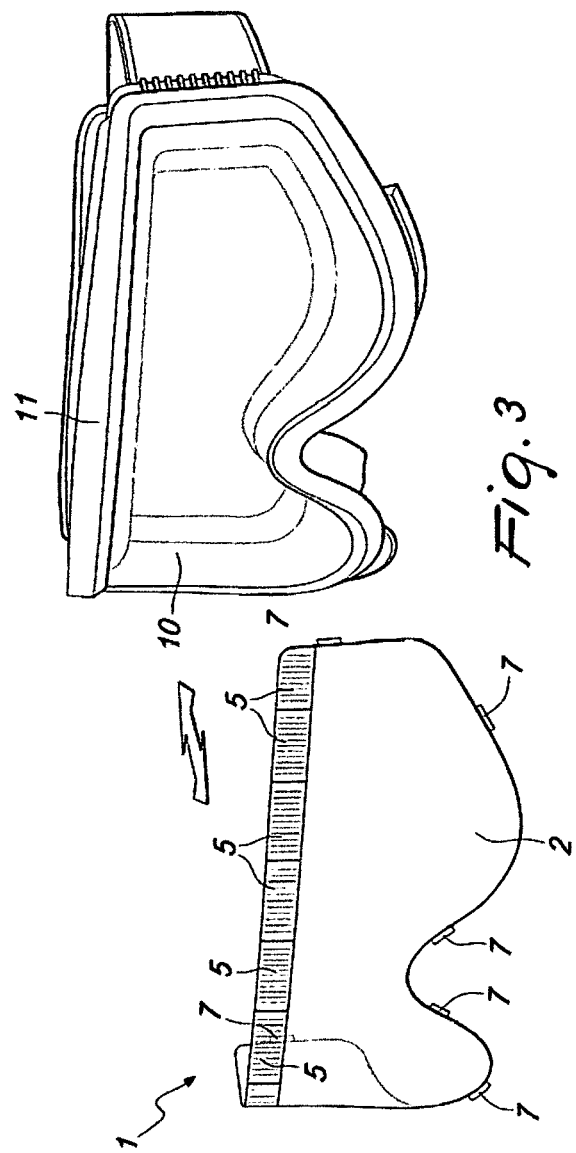
FIG. 3 visually represents, in a schematic prospective view, a protective screen, according to the invention, applicable on a pair of goggles.
Figure 4:
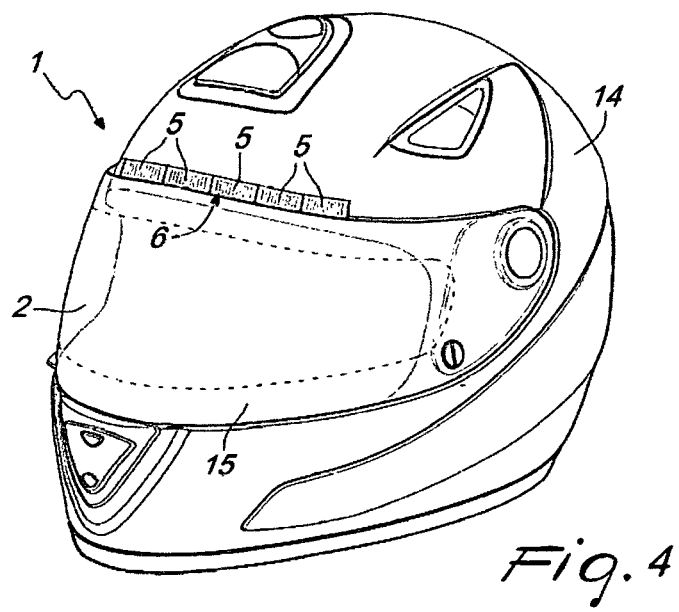
FIG. 4 visually represents, in a schematic prospective view, a protective screen, according to the invention, included in a protective helmet.
Figure 6:
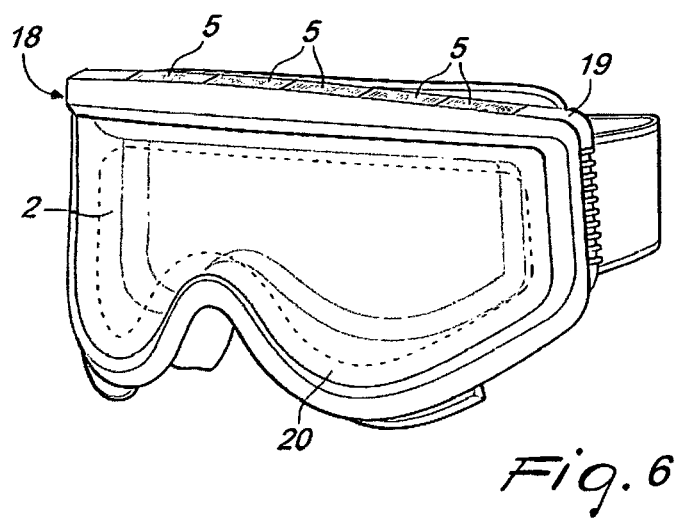
FIG. 6 visually represents, in a schematic prospective view, a protective screen, according to the invention, included in a pair of goggles.

For example, applying the invention on an helmet 14, the solar panel 6, constituted from the cells 5 is placed at the top of the helmet 14 itself, in the area that is directly contiguous with the visor 15 edge when this one is in the closed position. The visor 2 is the part of the visor 15 that is internal to the cross-hatched outline indicated in FIG. 2.

In the application of invention onto a pair of glasses 16, the solar panel 6 is placed on the top of the frame 17; the visors 2, that in this case obviously are two, are bounded to the lenses themselves (in particular embodiment, lens and visors 2, may be built up in a single element).

In the application of the invention onto a pair of goggles 18 (for example ski or snowboard goggles), the solar panel 6 is placed on the top of the frame 19; the visor 2 is coupled to the lens 20 itself (in particular embodiments, lens 20 and visor 2, may be built up in a single element). The visor 2 is the lens' part that is internal to the cross-hatched outline indicated in FIG. 2.

The functioning of the invention is intuitive, when the screen 1 is active the panel is invested by luminous radiations that causes the establishment of a certain difference of potential between his clips, proportionally to the intensity of the incident beam. The tension that is measurable at the clips of the panel 6, equal to the combination of every electromotive force of every single photovoltaic cell 5, is the voltage that supplies the liquid crystal visor. That visor 2, when correctly supplied, instantaneously darken, making the screen 1 to be dark, in order to alleviate the human eye from the nuisance produced from such an intense radiation.

When, after entering a tunnel, at dusk or in other situations crating the sudden reduction of the incident luminous beam, the voltage that can be measured at the clips of the solar panel 6 undergo a dramatic loss, and is not more enough to maintain the darkening condition of the liquid crystal visor 2. The visor 2 in such case will discharge, with a transitory phase as quick as greater will be the dissipation in the circuit; the electric charge in such case has the scope to speed up the transitory phase allowing the visor 2 to change state almost instantaneously constantly assuring a good sight to the user.

It is therefore clear how the invention achieve the suggested scopes.

The invention embodied this way is susceptible of numerous variations and modification all falling within the inventive concept field.

For example the electric charge could have adjustable value, in order to make possible to set up the brightness constituting the activation threshold of the whole system, or to put it better to set up the amount of light necessary to make the visor start functioning.

Alternatively a series of lithium-ion batteries can be used as a power source, substituting the 1.08MΩ) resistor with a photodiode.

Such photodiode act as a short-circuit when the incident light is scarce, depriving of the electrical supply the liquid crystal visor which so remain transparent, and act as an open switch when the incident light is intense, letting the voltage at the battery clips supply the visor which darken filtering the incident luminous beam.

A screen 1 according to the invention can positively be applied on glasses and generally on transparent surfaces to darken them as a function of the incident light on them.

It's to advise the possibility to insert in the circuit that is constituted by the panel 6 and the visor 2 also a light sensor to make the adjustment of the voltage that is supplied to the visor 2 (trough which are determined the transparency and the filtering action of the same) being done as a function of the lightness values detected by the sensor itself.

It's therefore easily applicable to vehicles' and buildings' glasses, as well as to glass dividing surfaces.

It's therefore prefigured the optional installation of batteries (or other electrical supply sources) to activate the darkening also in cases in which the external incident light is of poor intensity: this can be interesting for buildings' and/or vehicles" glasses as far as the need of darkening may not depend from sun protection's reasons, but from the necessity to protect the privacy of who is inside the installation's area of the screens 1.

The advantage of the screens 1 according to the invention is, as a matter of fact, that they can be affixed onto the still existing installation's surface: as any modification of the installation's surface is not necessary (the screen 1 is juxtaposed onto such surface whatever is its shape thanks to its flexibility) the assembly's costs will be minimum too, making the screen 1 according to the invention an object of great interest for a variety of applicative sectors.

Furthermore all the characteristics are substitutable with others technically equivalent.

Basically all the utilized materials, as well as sizes and shapes, could be whatever according to the needs, without exiting for this reason from the following claim's protection sphere.

The invention claimed is:

1. Protective re-usable and flexible material built screen of the type including a visor 2 containing a cell of a known liquid crystal or electro-chromic technologies, with variable transparency as a function of the electrical values measurable at its power supply clips 3, like but not exclusively ferro-electric, supper twisted nematics, dichroic dye gust-host where:

the liquid crystal visor 2 is characterized by the fact of being independent, autonomous and built with flexible materials that can be manually bended along several different axis in standard environmental conditions without significant loss of optical quality to match the surfaces of installation of a variety of existing see-trough screens, like but not exclusively "insert", "coating film" for existing face-shields, car glasses or goggles lenses, with the scope of enhance the hosting device comfort in the protection from the incident light;

the visor 2, in his preferred embodies, is characterized by the fact to be automatically controlled being activated in case of light, deactivated in case of darkness and fully supplied at the same time by one or more photovoltaic cell 5 connected in a serial or parallel circuit;

The visor 2 is power supplied by this photo-electric source with the possible interposition of a control circuit made of appropriate known electronic components 4 introduced with the sole purpose to better manage the electrical values of the power supplied.

2. The screen, as claimed in claim 1, is characterized in that its visor 2 comprises at least one layer of transparent and flexible material coupled with a liquid crystal or electro-chromic unit that could be bent without significant optical quality loss.

3. The screen, as claimed in claim 1, is characterized by the fact that the mentioned visor 2 comprises a couple of layers of bendable and transparent material with an interposed liquid crystal unit.

4. The screen, as claimed in claim 1, is characterized in that an additional high resistance resistor is putted in a parallel circuit with the power supply clips of the liquid crystal visor 2 in order to rapidly dissipate the energy accumulated by the mentioned visor 2 itself, restoring the initial conditions when the electric supply is missing.

* * * * *